(12) United States Patent
Tonelli et al.

(10) Patent No.: US 7,662,947 B2
(45) Date of Patent: Feb. 16, 2010

(54) ARABIDOPSIS-STOMATAL-SPECIFIC PROMOTER AND A GENETIC CONSTRUCT CONTAINING THE PROMOTER FOR EXPRESSION OF NUCLEIC ACIDS IN PLANTS

(75) Inventors: Chiara Tonelli, Milan (IT); Massimo Galbiati, Lomagna (IT)

(73) Assignee: Universita' degli Studi di Milano, Milan (IT)

( * ) Notice: Subject to any disclaimer, the term of this patent is extended or adjusted under 35 U.S.C. 154(b) by 139 days.

(21) Appl. No.: 10/590,490

(22) PCT Filed: Feb. 23, 2005

(86) PCT No.: PCT/EP2005/001883

§ 371 (c)(1),
(2), (4) Date: Jun. 25, 2007

(87) PCT Pub. No.: WO2005/085449

PCT Pub. Date: Sep. 15, 2005

(65) Prior Publication Data

US 2008/0064091 A1    Mar. 13, 2008

(30) Foreign Application Priority Data

Feb. 27, 2004    (IT)    ............ MI2004A0363

(51) Int. Cl.
  *C12N 15/82*    (2006.01)
  *C07H 21/04*    (2006.01)
  *C12N 5/04*    (2006.01)
  *A01H 5/00*    (2006.01)
(52) U.S. Cl. .............. 536/24.1; 800/287; 800/278; 800/298; 435/320.1; 435/419; 435/468
(58) Field of Classification Search .................. None
  See application file for complete search history.

(56) References Cited

U.S. PATENT DOCUMENTS 6,653,535 B1 * 11/2003 Tarczynski et al. ....... 800/320.1

FOREIGN PATENT DOCUMENTS

DE    19904754    *    8/2000

OTHER PUBLICATIONS

Donald et al. Mutation of either G box or I box sequences profoundly affects expression from the Arabidopsis rbcS-1A promoter. (1990) EMBO J. vol. 9; pp. 1717-1726.*
Benfey et al,. The cauliflower mosaic virus 35S promoter: combinatorial regulation of transcription in plants. (1990) Science; vol. 250; pp. 959-966.*
Kim et al. A 20 nucleotide upstream element is essential for the nopaline synthase (nos) promoter activity. (1994) Plant Mol. Biol. ; vol. 24; pp. 105-117.*
Maiti et al. Promoter/leader deletion analysis and plant expression vectors with the figwort mosaic virus (FMV) full length transcript (FLt) promoter containing single or double enhancer domains. (1997) Transgen. Res.; vol. 6; pp. 143-156.*
Doelling et al. The minimal ribosomal RNA gene promoter of Arabidopsis thaliana includes a critical element at the transcription initiation site. (1995) Plant J. vol. 8; pp. 683-692.*
Chen et al. Minimal regions in the Arabidopsis PISTILLATA promoter responsive to the APETALA2/PISTILLATA feedback control do not contain a CArG box. (2000) Sex. Plant Reprod. vol. 13; pp. 85-94.*
Database EMBL Online, Jan. 13, 1998, "Genomic sequence for Arabidopsis thaliana BAC F22013 from chromosome I, complete sequence." XP002343224.
Kranz Harald D et al: "Towards functional characterisation of the members of the R2R3-MYB gene family from Arabidopsis thaliana" Plant Journal, vol. 16, No. 2, Oct. 1998, pp. 263-276.
Cominelli E et al: "A Guard-Cell-Specific MYB Transcription Factor Regulates Stomal Movement and Plant Drought Tolerance" Current Biology, Current Science,, GB, vol. 15, No. 13, Jul. 12, 2005, pp. 1196-1200.

* cited by examiner

*Primary Examiner*—Cathy Kingdon Worley
(74) *Attorney, Agent, or Firm*—Young & Thompson

(57) ABSTRACT

The present invention relates to the expression of recombinant nucleic acids in plants. More specifically, the invention provides an *Arabidopsis* stomatal-specific promoter (At-MYB60 promoter—SEQ ID NO: 1)for the selective expression of nucleic acids in stomatal guard cells, gene constructs containing the promoter, expression vectors carrying such and plants transfected therewith. The selective expression of nucleic acids in plant guard cells allows the regulation of stomatal opening/closing states thereby modulating, e. g. increasing, the plant ability to resist to adverse environmental or climatic conditions.

18 Claims, 7 Drawing Sheets

SEQUENCE LISTING

<160> NUMBER OF SEQ ID NOS: 19

<210> SEQ ID NO 1
<211> LENGTH: 1291
<212> TYPE: DNA
<213> ORGANISM: Arabidopsis thaliana

<400> SEQUENCE: 1

| | | | | | | |
|---|---|---|---|---|---|---|
| cacaaggaca | caaggacata | tggtatgatg | atatgctttg | tttctctgct | tctcttacta | 60 |
| atttgaagct | gttggattga | tttgtctctt | cttacgttcc | cttcttttt | ttttcgtttt | 120 |
| cttttgtcgt | atagaccagg | cagggctag | ggcctagtga | tgggtattgg | cccaatacta | 180 |
| ttgggttatt | tgcctggttt | attatttcga | ttttaggtta | attcaatttt | aagaatacgt | 240 |
| agatttgttt | ggtttagttt | ggtttggttg | cactaagttc | ggttttacat | aaatagaatc | 300 |
| taacactact | aattgttata | cgtaaaatac | aacaacaata | acagattttt | cgtttcaatt | 360 |
| ttcgtttaag | agggtagaca | ttttggtttg | gtttggttca | ttttttttt | cccttcaaa | 420 |
| ttcacatcct | tcacgtagat | gacaaaataa | agaaaaacat | gaatgaaagt | tgtaacttgt | 480 |
| aagcatcaac | atggaaatca | tatcacaaag | aacacaaatc | taactaatgg | gtcttttcac | 540 |
| atattggtat | aattataagt | tgtaagaata | ttagttaaac | agaggcaacg | agagatgcgt | 600 |
| gatatatgaa | aagttgaaaa | caaagacat | ggatctaaag | agtcaagcaa | aatgtaatat | 660 |
| ctttttttct | tctaaacttg | aggatgtcca | agttgcagtg | aatgattccc | tttaatcatg | 720 |
| gagaaattca | atgaaataat | tgtgtttctt | cccacacttt | atctttattt | attttcttac | 780 |

| | |
|---|---|
| cacaattaca actattatca caaaaatgta agtaacatag cttgtgactc ttcttccatt | 840 |
| tatgagttga ttatcactat atttataagt aattaccaac gaatgttcca aattaagcaa | 900 |
| aatattgtaa tcgatacact atgtattcat ctacaatatg ttaacgagct ccttttatgg | 960 |
| aaatatttcg attgaaaaaa catttgatgg atcgttcact aaataaataa tccagtaacg | 1020 |
| ttttcttaag ggagatatac atattcgtgt ggagatcaac atatcttcgt taattgacta | 1080 |
| cgcaaaatag ttaatggaaa aggcagagtg actcgtgagc ttggcagatc caaaagaggt | 1140 |
| tgtcaagaaa aagcagattt aaaagttctt ccctcttctt taagtcaccc attaatttca | 1200 |
| catatatgta catacatgtt gcatttaact catatacata catattctca catctataaa | 1260 |
| gagagcataa gactcagaga gatctagagg a | 1291 |

```
<210> SEQ ID NO 2
<211> LENGTH: 246
<212> TYPE: DNA
<213> ORGANISM: Arabidopsis thaliana

<400> SEQUENCE: 2
```

| | |
|---|---|
| cgtgtggaga tcaacatatc ttcgttaatt gactacgcaa atagttaat ggaaaaggca | 60 |
| gagtgactcg tgagcttggc agatccaaaa gaggttgtca agaaaagca gatttaaaag | 120 |
| ttcttccctc ttctttaagt cacccattaa tttcacatat atgtacatac atgttgcatt | 180 |
| taactcatat acatacatat tctcacatct ataaagagag cataagactc agagagatct | 240 |
| agagga | 246 |

```
<210> SEQ ID NO 3
<211> LENGTH: 603
<212> TYPE: DNA
<213> ORGANISM: Arabidopsis thaliana

<400> SEQUENCE: 3
```

| | |
|---|---|
| caagttgcag tgaatgattc cctttaatca tggagaaatt caatgaaata attgtgtttc | 60 |
| ttcccacact ttatctttat ttattttctt accacaatta caactattat cacaaaaatg | 120 |
| taagtaacat agcttgtgac tcttcttcca tttatgagtt gattatcact atatttataa | 180 |
| gtaattacca acgaatgttc caaattaagc aaaatattgt aatcgataca ctatgtattc | 240 |
| atctacaata tgttaacgag ctccttttat ggaaatattt cgattgaaaa aacatttgat | 300 |
| ggatcgttca ctaaataaat aatccagtaa cgttttctta agggagatat acatattcgt | 360 |
| gtggagatca acatatcttc gttaattgac tacgcaaaat agttaatgga aaaggcagag | 420 |
| tgactcgtga gcttggcaga tccaaaagag gttgtcaaga aaaagcagat ttaaaagttc | 480 |
| ttccctcttc tttaagtcac ccattaattt cacatatatg tacatacatg ttgcatttaa | 540 |
| ctcatataca tacatattct cacatctata agagagcat aagactcaga gagatctaga | 600 |
| gga | 603 |

```
<210> SEQ ID NO 4
<211> LENGTH: 999
<212> TYPE: DNA
<213> ORGANISM: Arabidopsis thaliana

<400> SEQUENCE: 4
```

| | |
|---|---|
| atagaatcta acactactaa ttgttatacg taaaatacaa caacaataac agattttcg | 60 |
| tttcaatttt cgtttaagag ggtagacatt ttggtttggt ttggttcatt ttttttttcc | 120 |

```
ctttcaaatt cacatccttc acgtagatga caaaataaag aaaaacatga atgaaagttg      180
taacttgtaa gcatcaacat ggaaatcata tcacaaagaa cacaaatcta actaatgggt      240
cttttcacat attggtataa ttataagttg taagaatatt agttaaacag aggcaacgag      300
agatgcgtga tatatgaaaa gttgaaaaca aaagacatgg atctaaagag tcaagcaaaa      360
tgtaatatct ttttttcttc taaacttgag gatgtccaag ttgcagtgaa tgattccctt      420
taatcatgga gaaattcaat gaaataattg tgtttcttcc cacactttat ctttatttat      480
tttcttacca caattacaac tattatcaca aaaatgtaag taacatagct tgtgactctt      540
cttccattta tgagttgatt atcactatat ttataagtaa ttaccaacga atgttccaaa      600
ttaagcaaaa tattgtaatc gatacactat gtattcatct acaatatgtt aacgagctcc      660
ttttatggaa atatttcgat tgaaaaaaca tttgatggat cgttcactaa ataaataatc      720
cagtaacgtt ttcttaaggg agatatacat attcgtgtgg agatcaacat atcttcgtta      780
attgactacg caaaatagtt aatggaaaag gcagagtgac tcgtgagctt ggcagatcca      840
aaagaggttg tcaagaaaaa gcagatttaa aagttcttcc ctcttcttta agtcacccat      900
taatttcaca tatatgtaca tacatgttgc atttaactca tatacataca tattctcaca      960
tctataaaga gagcataaga ctcagagaga tctagagga                             999
```

```
<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcggatcctc tagatctctc tg                                                22

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aagcttcaca aggacacaag gaca                                              24

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atagaatcta acactactaa ttgttat                                           27

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
```

```
aagcttcaag ttgcagtgaa tga                                         23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aagcttcgtg tggagatcaa cat                                         23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aagcttgcag agtgactcgt ga                                          22

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cacttgatgg agctctctaa tatg                                        24

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctgcagacgt ttgtctagta g                                           21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctcatggccg ccggatcttg a                                           21

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
```

-continued cttgtctctc catatcttga gca                              23

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggagaagaac ttttcactgg agttgtccc                        29

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tagttcatcc atgccatgtg taatcccagc                       30

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aataacggtt caggcacagc                                  20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctgtggaatt gatcagcgtt g                                21

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gggaattcgt cgacaagc                                    18

ARABIDOPSIS-STOMATAL-SPECIFIC PROMOTER AND A GENETIC CONSTRUCT CONTAINING THE PROMOTER FOR EXPRESSION OF NUCLEIC ACIDS IN PLANTS

The present invention relates to the expression of recombinant nucleic acids in plants. More specifically the invention provides a promoter for the selective expression of nucleic acids in stomatal guard cells, gene constructs containing said promoter, expression vectors carrying them and plants transfected therewith. The selective expression of nucleic acids in plant guard cells allows the regulation of stomatal opening/closing states thereby modulating, e.g. increasing, the plant ability to resist to adverse environmental or climatic conditions.

BACKGROUND OF THE INVENTION

Tissue-Specific Promoters for the Generation of Transgenic Plants

The recent advancements in plant transformation techniques offer new opportunities to the improvement of crops. Following the transgenic approach, new characters can be introduced in the plants, which contribute to the increase of plant productivity, product quality and to improve the resistance of plants to adverse climatic conditions as well as to pathogens. In addition, transgenic plants can be used to produce recombinant proteins, biopolymers, medicaments, vaccines or antibodies (L. Lanfranco, Riv Biol. 2003, 96:31-54; Dunwell J M, J. Exp. Bot., 2000, 51:487-496).

The production of recombinant proteins in plants requires the use of promoters able to direct the correct expression of transgenes in vegetal tissues. To date, a limited number of promoters have been proposed for use in the generation of transgenic plants. Most of them are constitutive promoters, such as the 35S promoter from the cauliflower mosaic virus (CaMV35S) (Odell et al., Nature, 1985, 313:810-812) or the ubiquitin promoter (Holtorf et al., Plant Mol. Biol., 1995, 29:637-646).

A drawback of such promoters is that they are active in nearly all the plant tissues, thus preventing selective transgene expression in specific organs or during particular growth stages of the transgenic lineage, unlike tissue-specific promoters, which direct the production of recombinant proteins in selected tissues or organs. For example, the promoters involved in the accumulation of spare substances in seeds, such as phaseolina (Bustos et al., Plant Cell, 1989, 1:839-853) or 2S albumin (Joseffson et al., J. Biol. Chem., 1987, 262: 12196-12201), direct the seed-specific expression of transgenes. The Rubisco small subunit promoter or the potato ST-LSI promoter direct leaf-specific transgene expression (Stockhouse et al., EMBO J., 1989, 8:2445). Although many other tissue- or organ-specific promoters have been described in the literature, only few of them show selectivity for a determined plant cell-type. These promoters should direct transgene expression limited to particular cells within the plant organ.

Stomata: Anatomy and Function

Stomata are small apertures present on the surface of aerial organs of land plants. These structures play an important role in the regulation of gas fluxes between the plant tissues and the atmosphere, allowing either $CO_2$ influx, which is necessary for the photosynthesis, or water loss by transpiration. The stoma consists of two highly specialized epidermal cells, called guard cells, the movement of which determines the opening/closure of the stomatal rima (FIG. 1).

The level of stomatal opening reflects the balance between the need of $CO_2$ for the photosynthesis and water availability. Thus, it is not surprising that land plants have developed complex regulation mechanisms modulating the stomatal opening/closing process in response to environmental stimuli or to endogenous signals (Wilmer and Fricker, 1996, Stomata, Ed Chapman and Hall, London, 1-375).

The guard cell shape is determined by volume changes induced by turgor modifications. The latter are in turn induced by the exchange of solutes, either inorganic, such as $K^+$ and $Cl^-$, or organic, such as saccharose or malate, in the cell lumen (Schroeder et al., Ann. Rev. Plant Physiol. Plant Mol. Biol., 2001, 52:627-6658). Conditions favouring the photosynthetic activity, such as the presence of light and of elevated $CO_2$ concentrations, promote the accumulation of solutes in the guard cells, whereby an increased turgor induces stomatal opening (FIG. 1A).

On the contrary, in the absence of water, the phytohormon abscisic acid (ABA), induces a rapid diminution of guard cell turgor, resulting from the efflux of $K^+$, $Cl^-$ and saccharose and from the conversion of malate into osmotic-inactive starch, thereby causing stomatal closure (FIG. 1B).

The reduction of stomatal aperture, mediated by ABA accumulation, represents the main adaptive response of plants to drought, allowing to minimize the loss of water by transpiration (Wilkinson and Davies, Plant Cell Env., 2002, 25:195-210). Recently, many components of the ABA signal transduction cascade have been identified in guard cells following a pharmacological or genetic approach.

The ABA-induced stomatal closure involves the increase of $Ca^{++}$ cytosolic concentration, the activation of anion channels, the modification of cytoplasmic pH and of potassium channel activity, the production of oxygen reactive molecules, the regulation of phosphatases and kinases and of other proteins such as heterotrimeric G-proteins, farnesyltransferase and mRNA cap-binding protein (Schroeder et al, Ann. Rev. Plant Physiol. Plant Mol. Biol., 2001, 52:627-6658).

The modulation of hormon signal transduction mechanisms, having a direct influence on stomatal opening/closure, provides a valuable tool for the generation of crop plants resistant to adverse environmental or climatic conditions, expecially to drought, and in which the exchange of $CO_2$, and therefore the photosynthetic process, is optimized.

STATE OF THE ART

The modulation of ABA-induced signal transduction in the stomata enables the modification of the physiological response of guard cells to environmental stimuli. Many of the components involved in the mechanism of stomatal closure are known. Nonetheless, the modification of stomata activity is limited by the low availability of promoters specific for the guard cells.

Although a number of promoter sequences exerting their function in the guard cells have been described in the literature, none of them has shown sufficient selectivity. The promoters of *Arabidopsis* genes involved in the regulation of stomatal aperture, such as Osm1 (Zhu et al., Plant Cell, 2002, 14:3009-3028), Abh1 (Hugouvieux et al., Cell, 2001, 106: 477-487), Rac1 (Lemichez et al., Genes Dev., 2001, 15:1808-1816), Kat1 (Anderson et al., Proc. Natl. Acd. Sci. U.S.A., 1992, 89:3736-3740), Ost1 (Mustilli et al., Plant Cell, 2002, 14:3089-3099), Chl1 (Guo et al., Plant Cell, 2001, 13:1761-1777), have showed activity not only in guard cells, but also in different cell types and plant organs. The lack of selectivity prevents the use of such promoters in the generation of transgenic plants with modified stomatal activity.

Besides modulating stomatal closure, ABA regulates many aspects of plant physiology and growth, including seed latency, the synthesis of storage proteins and lipids, phase transition and the response to wounds or pathogens (Finkelstein et al., Plant Cell, 2002, S15-S45).

The use of a specific promoters for the ectopic expression of hormon signal transduction modulators may induce an altered response in different plant tissues and organs, including stomatal guard cells. As a consequence, defects and abnormalities may arise, negatively affecting plant physiology, growth and productivity.

DESCRIPTION OF THE INVENTION

The invention provides a method for the selective expression of nucleic acids in plant stomatal guard cells by using promoter sequences of the AtMYB60 gene (At1g08810; cDNA sequence deposited at GenBank acc. no. AF062895). In particular, the invention is based on the finding that different regions of AtMYB60 promoter enable either ABA-responsive or ABA-independent selective expression of nucleic acids in stomatal guard cells.

According to a first embodiment, the invention provides a genetic construct or cassette for the selective expression of a nucleic acid sequence in plant stomatal guard cells, said construct or cassette containing the nucleic acid sequence functionally linked to the promoter sequence of AtMYB60 gene (SEQ ID N. 1), or to fragments or variants thereof, said variants having at least 80%, preferably at least 90%, more preferably at least 95% sequence identity to SEQ ID No. 1, provided that said fragments or variants retain promoter activity on nucleic acid transcription.

According to preferred embodiments, the construct or cassette of the invention contains a fragment of the full-length AtMYB60 promoter sequence (SEQ ID No. 1), which is selected from the group consisting of SEQ ID N. 2 (from nucleotide (nt) 1045 to 1291 of SEQ ID N. 1), SEQ ID N. 3 (nt 689-1291 of SEQ ID N. 1) and SEQ ID N. 4 (nt 293-1292 of SEQ ID N. 1).

Whereas the fragment extending from nt 1045 to nt 1291 of SEQ ID N. 1 exhibits an ABA-independent promoter activity, the activity of larger fragments, particularly those containing SEQ ID N. 3 and 4, as well as the activity of the full-length promoter (SEQ ID N. 1), are down-regulated by abscisic acid. Therefore, the stoma-specific expression of nucleic acids can be modulated in either ABA-dependent or ABA-independent manner using different gene constructs or expression cassettes according to the invention.

Besides the region of the AtMYB60 gene endowed with transcription-promoter activity, the expression cassette or constructs of the invention may contain genetic elements involved in transcription regulation, such as introns, polyadenylation sites at the gene 3'-end, transcription activators or enhancers, termination sequences, selection markers and leader sequences.

Any nucleic acid can be operatively linked to the AtMYB60 promoter and inserted in the cassette or construct according to the invention. In particular, both coding and non-coding sequences can be used in the construction of the expression cassette. The encoded product, whether a peptide, protein or RNA transcript, is preferably involved in the intracellular signalling pathway modulated by abscisic acid (ABA) and in the cellular mechanisms regulating the stoma opening/closure state.

According to preferred embodiments of the invention, the AtMYB60 promoter, fragments or variants thereof, are functionally linked to i) genes involved in the control of stomata aperture, in particular the Osm1, Rac1, Kat1, Ost1 and Chl1 genes (see above for the respective bibliographic references), ii) genes involved in the control of light-induced stomatal opening, particularly the guard cell blue-light photoreceptors PHOT1 and PHOT2 (Kinoshita T et al., Nature. 2001, 414: 656-60), genes encoding for 14-3-3 proteins (Baunsgaard L et al., Plant J. 1998, 13:661-71), and the dual-affinity nitrate transporter gene AtNRT1.1 (CHL1 ) (Guo F Q et al., Plant Cell. 2003, 15:107-17), iii) genes involved in the control of ABA-induced stomatal closure, particularly genes encoding for the following proteins: the type 2C protein phosphatases ABI, ABI2 and AtP2C-HA (Leung J et al., Plant Cell. 1997, 9:759-71.; Leonhardt N et al., Plant Cell. 2004, 16:596-615), the PP2A protein phosphatase RCN1 (Kwak J M et al., Plant Cell. 2002, 14:2849-61), the AAPK $Ca^{2+}$-independent protein kinase OST1 (Mustilli A C et al., J. Plant Cell. 2002, 14:3089-99), the SOS3-like calcium binding protein SCaBP5 and its interacting protein kinase PKS3 (Guo Y et al., Dev Cell. 2002, 3:233-44), the AtrbohD and AtrbohF NADPH oxidases (Kwak, J. M. et al., EMBO J., 2003, 22:2623-33), the GTPase AtRac1 (Lemichez E et al., Genes Dev. 2001, 15:1808-16), the GTP-binding protein alpha subunit GPA1 (Wang X Q et al., Science. 2001, 29:292:2070-2), the syntaxin OSM1/SYP61 (Zhu, J. et al., Plant Cell, 2002, 14: 3009-28), the farnesyltransferase beta subunit ERA1 (Pei Z M et al., Science. 1998,282:287-90), the nitrate reductase NIA1 and NIA2 (Desikan R et al., Proc Natl Acad Sci U S A. 2002, 99:16314-8), $K^+_{in}$ channels KAT1, KAT2, AKT2 (Kwak J M et al., Plant Physiol. 2001, 127:473-85), the $K^+_{out}$ channels GORK (Hosy E et al., Proc Natl Acad Sci U S A. 2003, 100:5549-54), the nuclear RNA cap binding complex ABH1 subunit (Hugouvieux V et al., Cell. 2001, 106:477-87), the Sm-like snRNP protein SAD1 (Xiong L et al., Dev Cell. 2001, 1:771-81), and the homeobox-leucine zipper transcription factor ATHB6 (Himmelbach A et al., Grill E., EMBO J. 2002, 21:3029-38).

Alternatively, nucleic acid sequences controlling the production of RNA transcripts exerting specific functions in the host cell, in particular antisense RNAs and siRNAs, can be inserted in the cassette or construct according to the invention.

As used herein, the expressions "funtionally linked" and "operatively linked" indicate that the promoter and nucleic acid making up the cassette or construct according to the invention, are in such a reciprocal orientation as to allow the promoter directing the expression of the nucleic acid, generally in 5'-3' orientation.

In a further aspect, the invention relates to expression vectors carrying the gene constructs or cassettes herein provided. The vectors can be bacterial plasmids, bacterial artificial chromosomes (BACs), yeast artificial chromosomes (YACs), viral vectors, vectors for direct DNA transfer, or, preferably, vectors for *Agrobacterium*-mediated DNA transfer. The latter can be either integrating or binary vectors and may contain selection markers, such as antibiotic- or herbicide-resistance genes, reporter genes facilitating the identification and selection of transformed cells, or sequences regulating gene expression in plants.

Direct transfer of DNA may include protoplast microinjection, electroporation and biolistic techniques based on plant bombardment with DNA-coated microparticles.

In a further aspect the invention provides transgenic plants, either monocotyledonous or dicotyledonous, as well as vegetative or reproductive parts thereof, or seeds, containing the genetic constructs according to the invention. In a preferred embodiment, the constructs or cassettes according to the invention are used to express proteins in the guard cell of closely related crop species, such as canola, in other dicotyledon plant, including soybean, tomato, tobacco, potato, cotton, or in monocotyledon species, such as corn, wheat, barley, rice.

The procedures for transforming plants with transgenic vectors or with naked DNA are known to those skilled in the art. For example, seeds at the germinative stage, seedlings or adult plants can be inoculated with *Agrobacterium* carrying the heterologous gene construct, and grown in suitable conditions.

The possibility of finely regulating stoma functions provides an important tool for the generation of plants able to efficiently respond to climatic changes. In particular, the possibility of inhibiting ABA-stimulated response thereby increasing the degree of stomatal opening and, consequently, the influx of $CO_2$ required for the photosynthetic process, is particularly important for plants cultivated in areas where water is not an environmental limiting factor. On the contrary, reducing stomatal aperture to avoid loss of water by transpiration is particularly beneficial to plants cultivated in dry areas.

DETAILED DESCRIPTION OF THE INVENTION

Characterization of AtMYB60 Promoter Sequence

AtMYB60 is a member of the large family of R2-R3 MYB transcription factors of *Arabidopsis*. To examine the expression profile in wild-type *Arabidopsis* plants grown in standard conditions, different portions of the intergenic regions located either upstream of the translation initiation codon or downstream of the stop codon, were cloned upstream and, respectively, downstream the GFP (Green Fluorescence Protein) and GUS (β-glucuronidase) reporter genes (FIG. 2B).

The constructs thus obtained were introduced in *Arabidopsis* and the resulting transgenic lines were histologically analyzed to detect the reporter expression domains. In all the samples examined, reporter gene expression was only detected in guard cells from all plant aerial organs provided with stomata (FIGS. 3-6).

Lines Transformed with p1.3-2.2:GUS Construct

The complementary and inverted sequence corresponding to the genomic region of Chromosome 1 comprised between nt 2821639 (3'UTR sequence of At1g08820 gene) and nt 2820349 (3'UTR sequence of AtMYB60 gene-At1g08810)—according to the nomenclature used in "The *Arabidopsis* Information Resource" accessible at http://www.arabidopsis.org—was cloned upstream of the GUS reporter gene (FIG. 2A, B, and FIG. 7).

The intergenic region downstream of AtMYB60 and comprised between the stop codon and the 5'UTR region of At1g08800 was inserted downstream of the same GUS reporter gene (FIG. 2A, B). The genomic regions used in this construct contain the entire AtMYB60 promoter and the putative regulatory elements located in the 3' region.

Subsequently, T2 plants obtained by transformation with the p1.3-2.2:GUS construct were analyzed to determine the expression profile of the reporter gene. GUS staining was only found in stomatal guard cells from all the plant organs provided with such anatomical structures and at any growth stage (FIG. 3). Hereinbelow, a detailed description of the results relating to different parts of the plant and to different growth stages are reported.

Seedling

Seedlings were analysed at days 4 and 7, i.e. at the stage of expanded cotyledon and at the moment of leaf appearance, respectively. A strong GUS-staining was observed at the level of stomatal guard cell, in both cotyledons and primary leaves, and in the hypocotyl (FIG. 3). No staining was detected in the primary root and in its side branches.

Adult Plant

The vegetative and reproductive organs were analysed in 7-week plants. GUS staining was present in stomatal guard cells from basal rosette leaves, cauline leaves and stems (FIG. 4A, B, C).

As to the organs of the flower apparatus, GUS staining was detected in stomatal guard cells from sepals, pistils, anthers and in immature siliques (FIG. 4D, E, F, G). The observation of petals, where stomata are absent, did not reveal any staining.

Lines transformed with p1.3:GUS, p0.9:GFP, p0.6.:GUS, p0.2:GUS and p189:GUS constructs.

In order to confirm the results obtained from plants transformed with the p1.3-2.2:GUS construct and to delimit the genomic region necessary and sufficient for directing stam-specific expression of the reporter gene, the following constructs were prepared (FIG. 2B):

p1.3:GUS, containing the same intergenic region upstream of AtMYB60 as that used in p1.3-2.2 GUS, cloned in front of the GUS reporter;

p0.9:GFP, containing a 999 bp genomic fragment upstream of AtMYB60, cloned in front of the GFP reporter (the activity of which can be detected by means of confocal microscopy);

p0.6:GUS, containing a 603 bp genomic fragment upstream of AtMYB60, cloned in front of the GUS reporter;

p0.2:GUS, containing a 246 bp genomic fragment upstream of AtMYB60, cloned in front of the GUS reporter;

p189:GUS, containing a 189 bp genomic fragment upstream of AtMYB60, cloned in front of the GUS reporter.

As shown in FIG. 5, all the constructs analysed, with the only exception of p189:GUS, displayed the same expression profile as that obtained from plants transformed with p1.3-2.2:GUS construct. The presence of both reporter activities was observed solely in stomatal guard cells from all the seedling or plant structures provided with stomatal apertures.

In particular, the confocal-microscopy analysis of tissues from p0.9:GFP-transformed lines, clearly showed that the reporter expression was confined to stomatal guard cells, being the signal absent in any other cell-type (FIG. 6).

ABA-Induced Modulation of Reporter Gene Expression.

Recent studies have shown that the transcription regulation mediated by abscisic acid (ABA) represents an important control for stomatal physiological responses. Therefore, the effects of exogenous ABA administration on the expression of GUS and GFP reporter genes have been examined in the transgenic lines described above. The expression analysis was carried out with semiquantitative RT-PCR, and indicated that the levels of the GUS reporter transcript in p1.3-2.2:GUS. P1.3:GUS and p0.6:GUS lines, were significantly decreased by ABA administration (FIG. 7). The same result was confirmed with the GFP reporter in p0.9:GFP lines. On the contrary, no change in GUS expression was observed in p0:2GUS lines treated with ABA (FIG. 7). These results indicate that the expression of genes fused to the promoter of AtMYB60 (SEQ ID No. 1) is down-regulated by ABA. Further, the results indicated that the cis elements responsible for negative transcription modulation are contained between nucleotides −603 and −246, upstream of the translation initiation codon of AtMYB60.

Consequently, the entire promoter sequence SEQ ID No. 1, or fragments thereof containing the 246 bp portion upstream of the ATG codon, enable the ABA-independent expression of transgenes in stomatal guard cells.

Optical microscopy photographies of *Arabidopsis* stomata present on leaf surface (bar=5 µm). The stomata present on the epidermis of most of the aerial organs of soil plants are formed by two highly-specialized guard cells (g). Turgor changes in guard cells cause the aperture or the closure of the stomata rima.

FIG. 2

(A) Schematic representation of the genomic region containing the AtMYB60 gene. There are shown the end portion of the At1g08820-gene final exon, the three exons of the AtMYB60 (At1g08810) coding region, and the initial portion of the At1g08800 gene—first exon.

(B) Schematic representation of constructs containing the GUS and GFP reporter genes under the control of different portions of the intergenic region between At1g08820 and AtMYB60. The p1.3-2.2:GUS construct further contains the entire intergenic region comprised between AtMYB60 and At1g08800, inserted downstream of the GUS reporter. The length of each genomic region is indicated as number of bp.

Figure 1:
FIG. 1—Stomatal anatomy and function
Figure 2:
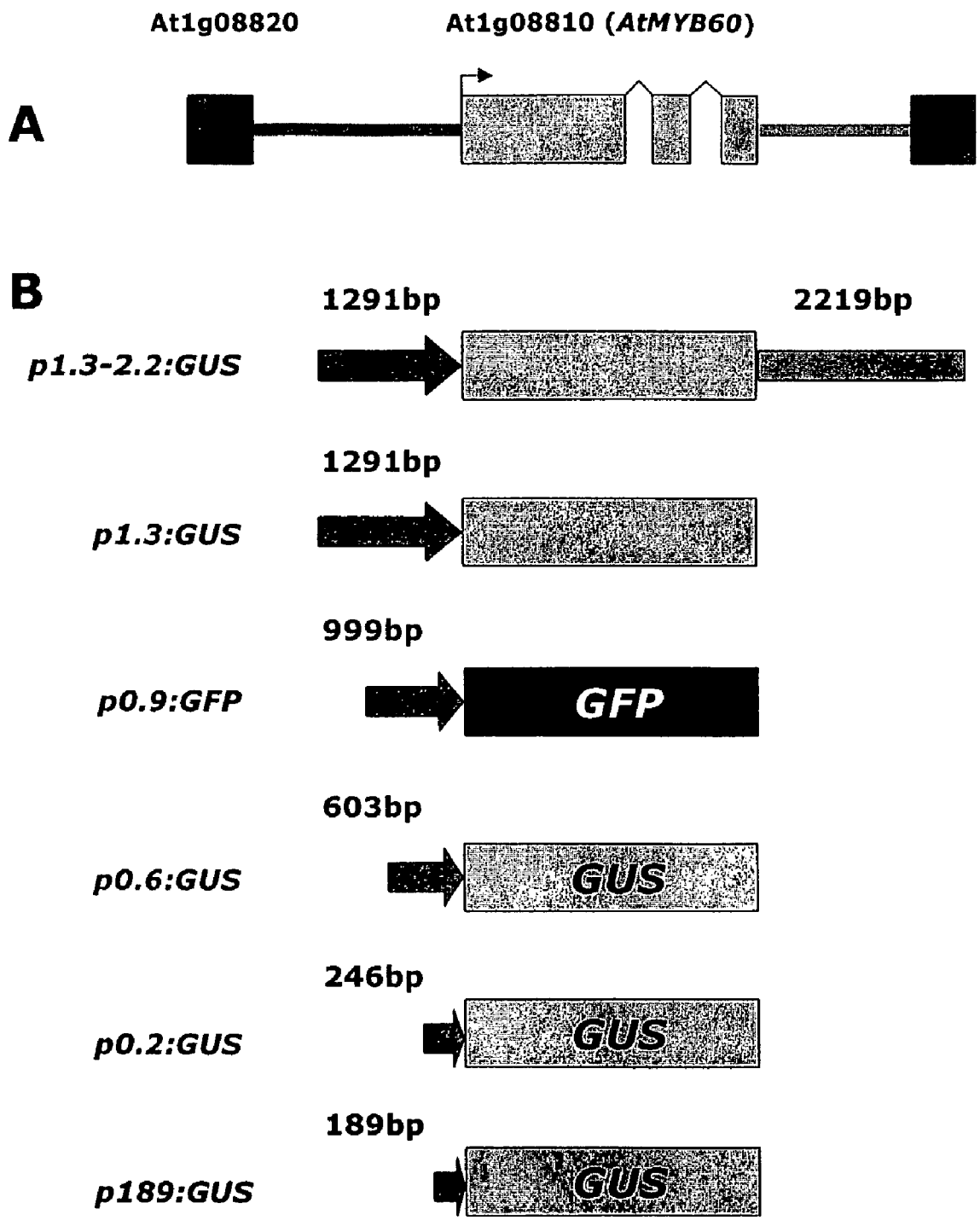
Figure 3:

FIG. 3—Stoma-specific expression of the GUS reporter in seedlings from lines transformed with the p1.3-2.2:GUS construct A) expression of the reporter GUS in seedlings at day 4. The staining is present only in stomatal guard cells in the cotyledons (c) and hypocotyl (i). No signal is found in the root (r).

B) cotyledon (particular)

C) leaf epidermis of a 7-day seedling (particular).

Figure 4:
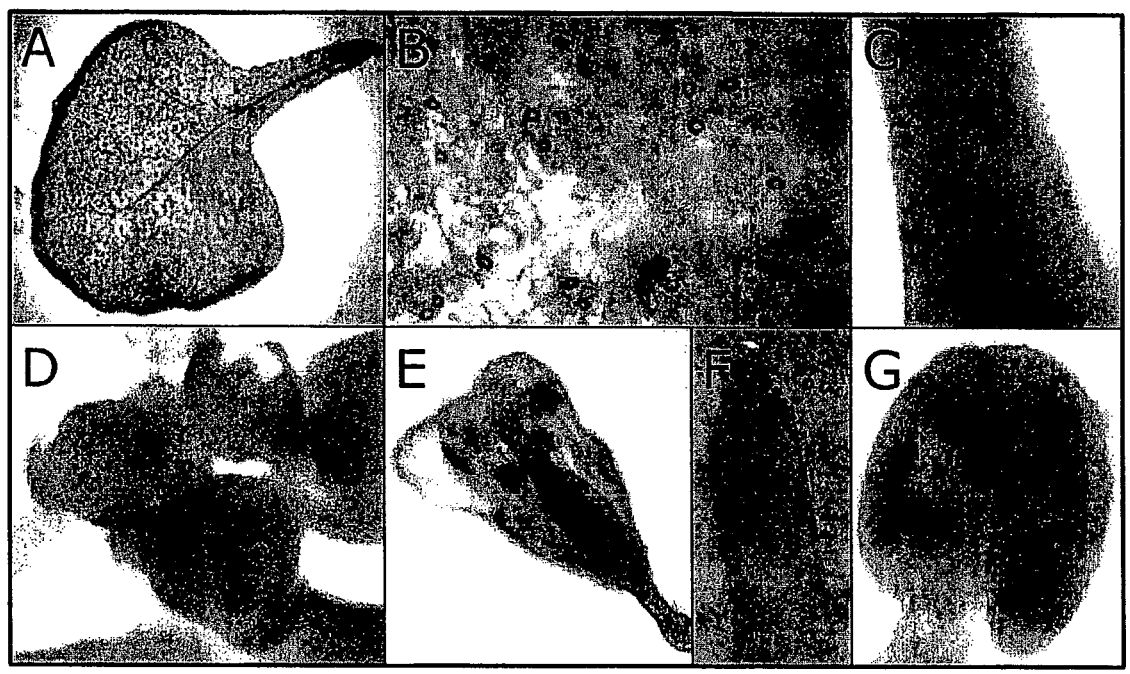

FIG. 4—stoma-specific expression of the GUS reporter in adult plants from lines transformed with the p1.3-2.2:GUS construct A) expression of the reporter GUS in leaves from 7-week adult plants B) leaf (particular)

C) stem (particular)

D) mature inflorescence: GUS staining is present only in the sepal stomata

E) mature flower: GUS staining is present only in sepal, anther and pistil stomata.

F) Pistil (particular)

G) Anther (particular)

Figure 5:
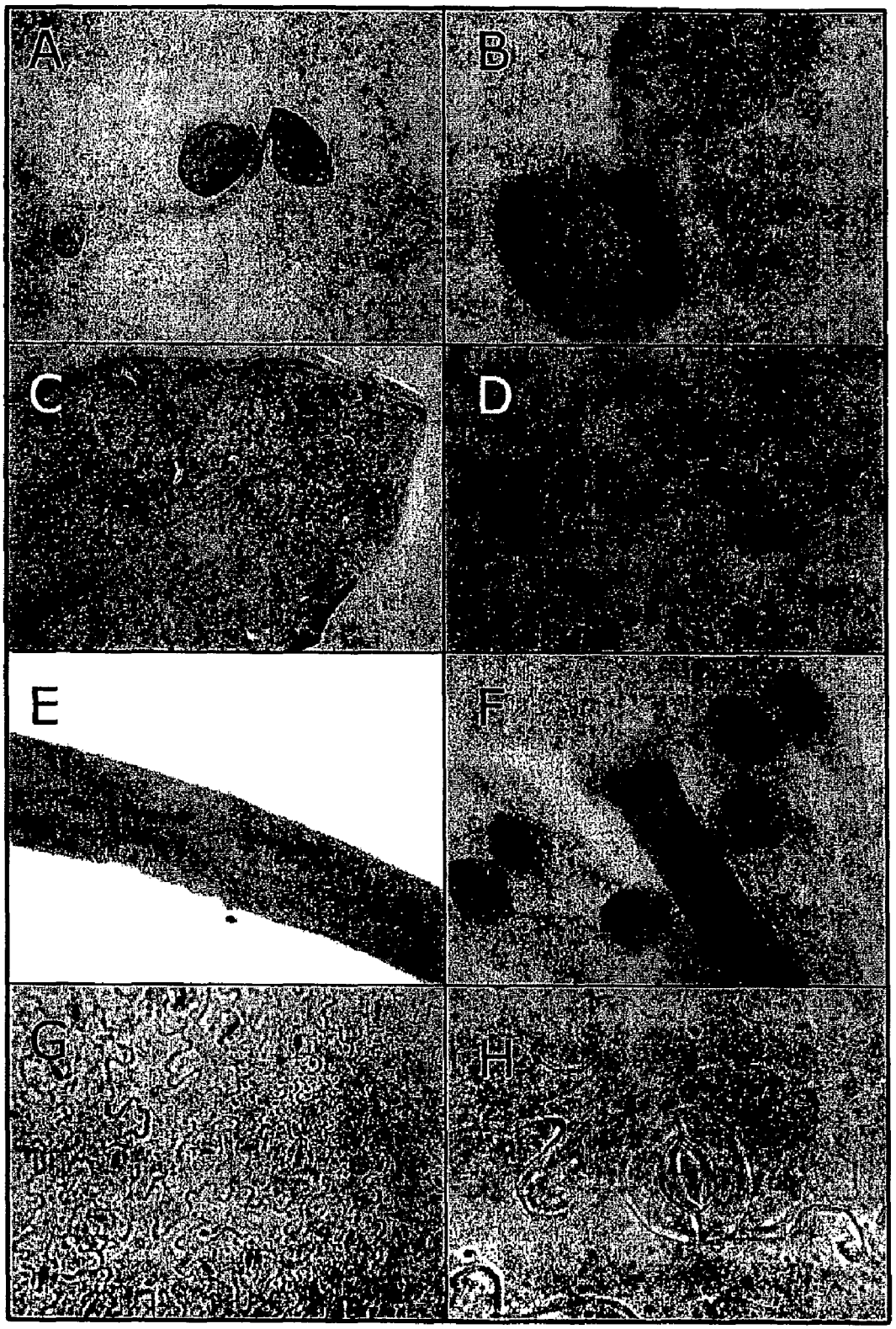

FIG. 5—expression of the GUS reporter in adult plants from lines transformed with p1.3:GUS, p0.6:GUS, p0.2:GUS and p189:GUS constructs Examples of staining of lines transformed with different constructs:

A) and B) 4-day seedling

C) rosette leaves

D) stem

F) mature flower

Figure 6:
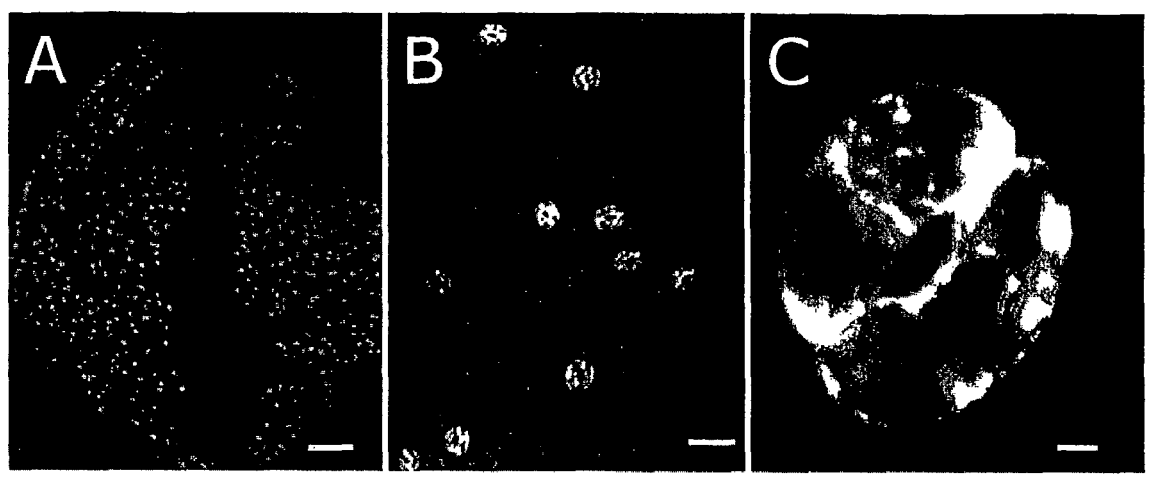

G) and H) rosette leaf stomata from plants transformed with the p189:GUS construct FIG. 6—stoma-specific expression of the GUS reporter in adult plants from lines transformed with the p0.9:GFP construct A) Expression of the GFP reporter in leaves from 7-week adult plants (bar=1 µm)

B) Expression of the GFP reporter in a stem examined by confocal microscopy (bar=20 µm)

C) Particular of a leaf stoma examined by confocal microscopy (bar=2 µm)

Figure 7:
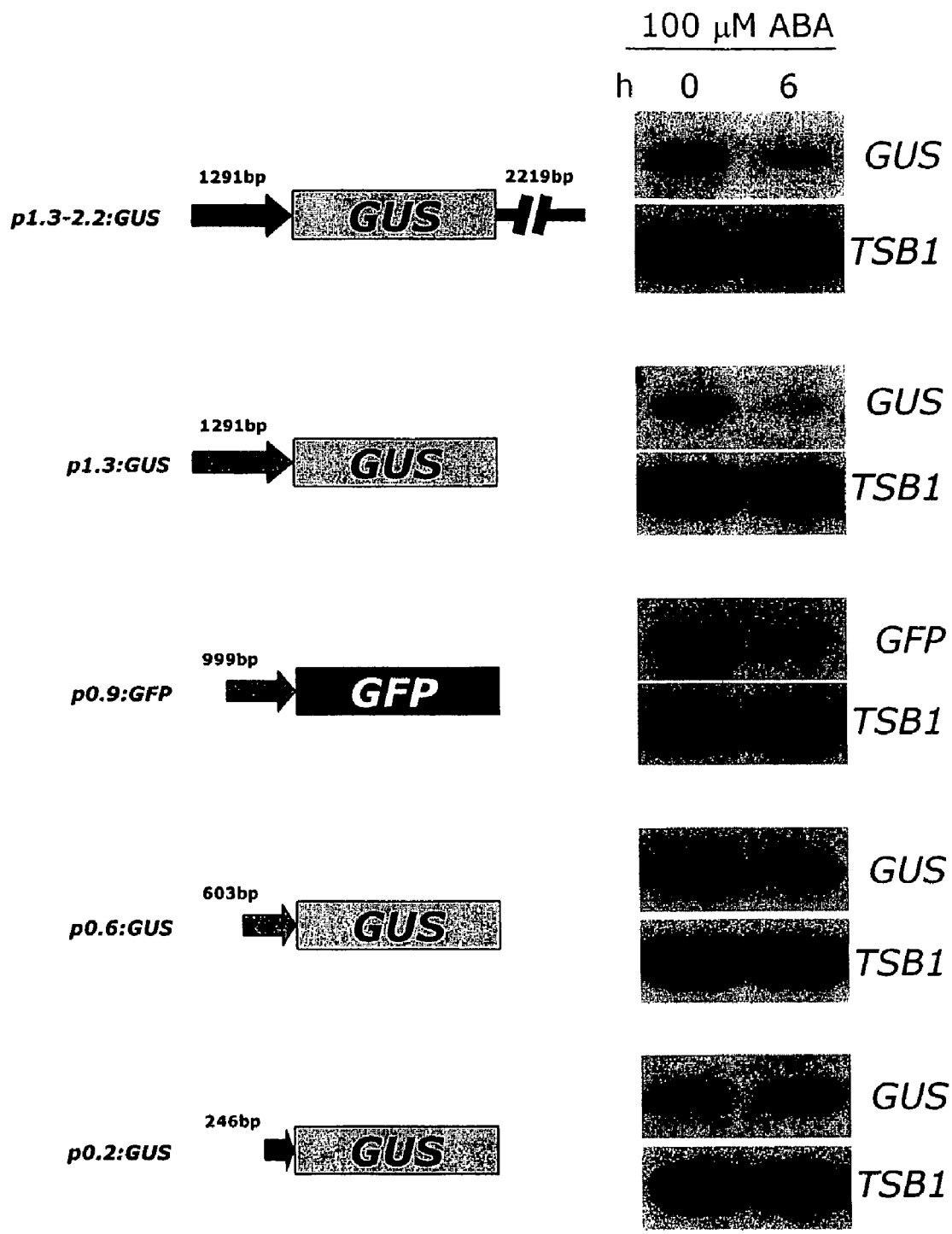

FIG. 7—expression of the GUS and GFP reporter in plants treated with ABA RT-PCR analysis of the GFP and GUS reporter expression in transgenic lines treated with 100 µM ABA for 6 hours. TSB1 gene is used as the control.

MATERIALS AND METHODS

Plant Growth

For in-plate growth, the seeds were sterilized as follows: 5 min in absolute ethanol, 5 min in 0.6% (v/v) sodium hypochlorite, 0.05% TWEEN 20, 2 washes in sterile water. The seeds were resuspended in 0.1% agarose sterile solution and germinated in Petri dishes containing 0.7% agarized MS medium (Sigma M-5519) added with 1% saccharose, pH 5.7. The plates were layered for 4 days at 4° C. in the dark to allow uniform germination and then placed at 22° C. with 16 hr light (48 µE/m$^2$) and 8 hr dark periods.

For the growth in soil, the seeds were layered at 4° C. in the dark for a period of 4 days and then germinated in Einheitserde soil (VM-type, Manna-Italy) in Araflat plates (Arasystem, Betatech, Belgium) or in culture bottles, with a 16 hr light (48 µE/m$^2$)-8 hr dark cycle.

Genomic DNA Extraction

Seedlings that were grown in plates, as well as flowers or leaves from plants grown in soil, were placed in EPPENDORF tubes and frozen in liquid nitrogen. The tissues were minced in the tubes, by means of a plastic tip fixed to a bench drill, in the presence of 500 µl extraction buffer (7M urea, 350 mM Na$_2$SO$_4$, 50 mM Tris pH 8.0, 8 mM EDTA, 34 mM sarkosyl). The same volume of phenol and chloroform was then added (1:1 v:v) and, after vortexing, the samples were centrifuged at 13000 rpm for 5 min. The supernatant was placed in clean tubes and added with 400 µl of distilled water and 0.7 volumes of isopropanol. The DNA was precipitated by centrifugation of the samples at 13000 rpm for 10 min. Isopropanol was removed and the pellet washed with 300 µl of 80% ethanol. After removal of ethanol, the DNA was resuspended in 40 µl of 50 mM Tris-HCl pH 8.0, 20 µg/ml of 5 mM EDTA.

Amplification of AtMYB60 5' and 3' Genomic Regions

The P69R5NEW primer (5' TCGGATCCTCTAGATCTCTCTG 3') (SEQ ID NO: 5) was used for the amplification of different portions of the region upstream of the AtMYB60 gene, in combination with the primers reported in the following Table. A BamHI restriction site (GGATCC) was introduced in the P60R5NEW primer.

| Primer | Sequence 5'-3' | Region amplified with P60F1 | Construct |
|---|---|---|---|
| P60F1 | AAGCTTCACAAGGACACAAGGACA (SEQ ID NO: 6) | 1291 bp | p1.3: GUS<br>p1.3-2.2: GUS |
| P60F8 | ATAGAATCTAACACTACTAATTGTTAT (SEQ ID NO: 7) | 999 bp | p.09: GFP |
| P60F2bis | AAGCTTCAAGTTGCAGTGAATGA (SEQ ID NO: 8) | 603 bp | p0.6: GUS |
| P60F3 | AAGCTTCGTGTGGAGATCAACAT (SEQ ID NO: 9) | 246 bp | p0.2: GUS |
| P60F5 | AAGCTTGCAGAGTGACTCGTGA (SEQ ID NO: 10) | 189 bp | P189: GUS |

The AAGCTT sequence corresponding to a HindIII restriction site, was inserted to facilitate the cloning of genomic fragments.

The 3' genomic region, 2219bp in length, was amplified using the primers 60-3'UTRF2 (5' CACTTGATGGAGCTCTCTAATATG 3') (SEQ ID NO: 11) and 60-3' UTRR1 (5' CTGCAGACGTTTGTCTAGTAG 3') (SEQ ID NO: 12).

The PCR reactions were carried out with 0.5 µg genomic DNA in a reaction mixture containing RED TAQ PCR Reaction Buffer 1× (Sigma), dATP, dCTP, dGTP and dTTP (5 mM each), primers (25 µM each), 1 unit RED TAQ polymerase (Sigma) and sterile distilled water to a final volume of 25 µl. The amplification reaction was performed as follows: 1 min at 94° C.; 40 cycles at 94° C. for 15 sec, 15 sec at the annealing temperature specific for the primer pair utilized, 72° C. for 1 min; 72° C. for 10 min. The reaction products were separated by electrophoresis on 1% (w/v) agarose gel in TBE 1× (89 mM Tris-base, 89 mM H2BO3, 2 mM EDTA pH 8) and analyzed with a UV transilluminator. The obtained bands were excised from the agarose gel and purified by means of QIAQUICK Gel Extraction Kit (Quiagen), according to the manufacturer's instructions.

Preparation of the Constructs Containing the Different Genomic Regions Fused to the Reporter Gene p0.9:GFP Construct The 999 bp genomic fragment was cloned in pCRII-TOPO vector (Invitrogen), according to the manufacturer's instructions. Subsequently, the fragment was excised by EcoRI cleavage and its ends were made non-sticky by treatment with Klenow (Roche), following the manufacturer's instructions. The fragment thus obtained was inserted in the binary vector pBIN mGFP-ER, containing the GFP reporter, previously digested with HindIII and treated with Klenow.

p1.3-2.2:GUS Construct

The 1291 bp genomic fragment was cloned in the pCR4-TOPO vector (Invitrogen), following the manufacturer's instructions. This fragment was subsequently excised by HindIII, BamHI cleavage and cloned in the HindIII, BamHI sites of the binary vector pBI101.3 (Stratagene), containing the GUS reporter, to produce the p1.3:GUS vector. The genomic fragment corresponding to the 3' region of AtMYB60, 2219 bp in length, was inserted in pCRII-TOPO vector and subsequently excised by EcoRI cleavage. The EcoRI fragment was then inserted in the EcoRI site downstream the transcription terminus of the p1.3:GUS vector, to generate the p1.3-2.2: GUS vector.

p0.6:GUS Construct

The genomic fragment of 603 bp was cloned in the pCR4-TOPO vector (Invitrogen), following the manufacturer's instructions. The fragment was subsequently excised by HindIII, BamHI cleavage and cloned in the HindIII, BamHI sites of vector pBI101.3 (Stratagene).

p0.2:GUS Construct

The 246 bp genomic fragment was cloned in pCR4-TOPO vector (Invitrogen), following the manufacturer's indications. The fragment was subsequently excised by HindIII, BamHI cleavage and cloned in the HindIII, BamHI sites of the pBI101.3 binary vector (Stratagene).

p189:GUS Construct

The 189 bp genomic fragment was cloned in pCR4-TOPO vector (Invitrogen), following the manufacturer's indications. The fragment was subsequently excised by HindIII, BamHI cleavage and cloned in the HindIII, BamHI sites of the pBI101.3 binary vector (Stratagene).

Plant Transformation

Wild-type *Arabidopsis thaliana* plants belonging to the Columbia ecotype were grown at 22° C. with a photoperiod of 16 hr light/8 hr dark. In order to increase seed production, the primary inflorescences were removed and the plants were grown for additional 5-6 days, until the secondary inflorescences appeared. All the siliques were eliminated prior to transformation. The plants were then transformed with the *Agrobacterium* strain GV3101 by "floral-dip", following the Clough-Bent protocol (Clough and Bent, Plant J., 1998, 16:735-743).

Sterilized T1 seeds from transgenic plants were layered at 4° C. in the dark for 4 days, and subsequently germinated in MS soil (Sigma M-5519), added with 0.8% BACTOAGAR (Difco 0141-01) pH 5.7 and 100 µg/ml kanamycin. The plants were grown at 22° C., under 16 hr light/8 hr dark photoperiod.

GUS Assay

Seedlings, rosette and stem leaves, stalks, inflorescences and siliques were placed in microtiter plate wells containing 2.0 ml GUS-staining solution (100 mM sodium phosphate pH 7.0, 0.1% Triton X-100, 1 mg/ml X-Gluc, 0.5 mM ferrocyanidine). The microtiter plate was placed in a vacuum-dryer for 10 min prior to incubation at 37° C. for one night in the dark. The GUS-staining solution was then removed and the tissues were washed several times with absolute ethanol for 1 hr, until complete removal of staining. The tissues were kept at −20° C. in 70% ethanol.

The reporter expression profiles were examined with the OLYMPUS SZX12 stereoscope (7×-90× magnification).

Confocal microscope analysis

Samples for confocal microscope analysis were placed in a glass slide provided with a cover (COVERWELL PERFUSION CHAMBER OBLONG—Sigma), and immersed in a solution containing 0.3% gelrite, 1% saccharose and ½ MS pH 5.8 (GELRITE GELLANGUM Sigma). Subsequently, a histology slide was placed over.

The analysis was carried out with a TCS NT confocal microscope (LEICA) equipped with Argon-Krypton laser carrying a filter for GFP (488 nm excitation, 519 nm emission). Scanning was repeated several times at different magnification.

ABA Treatment and RT-PCR Analysis

The seeds from different transgenic lines were sterilized as described above and germinated in liquid MS soil containing 1% saccharose and 0.5 gL$^{-1}$ MES. After three week growth under continuous shaking (120 rpm), ABA was added at a final concentration of 100 μM. The tissues for mRNA extraction were taken at time 0 and after 6 hr treatment. Total RNA was extracted by mincing the frozen tissues in 500 μl extraction buffer (1M Tris HCl pH 9, 20% Sodium Dodecyl Sulfate, 4M LiCl and 10 mM EDTA).

After phenol chloroform extraction, the RNA was precipitated at 4° C. in 4M LiCl, washed with 70% ethanol and resuspended in water treated with diethylpyrocarbonate (1% DEPC). 5 μg total RNA were treated for 30 min with DNASE I (15 units—Boheringer Mannheim), following the manufacturer's protocol. The reverse-transcription reaction was performed with REVERSE TRANSCRIPTASE SUPERSCRIPT II (Life Technologies), according to the manufacturer's indications, using the oligo(dT) primer, formed by 17 dT residues and by the adapter 5'-GGGAAT-TCGTCGACAAGC-3'. The cDNA samples were amplified in a reaction mixture containing RED TAQ PCR Reaction Buffer 1× (Sigma) and 5 mM dATP, dCTP, dGTP and dTTP, 25 μM specific primers (Table below), 1 unit RED TAQ polymerase (Sigma) and sterile distilled water to a final volume of 25 μl. The amplification was carried out under the following conditions: 1 min at 94° C.; 20 cycles at 94° C. for 15 sec, 60° C. for 15 sec, 72° C. for 1 min; 72° C. for 10 min. The PCR products were separated on 1% agarose gel and transferred to HYBOND N+ filters (Amersham) in 0.4N NaOH. Filters were hybridized with TSB1-, GUS- or GFP-specific probes amplified using the primers indicated in the Table below, and tagged with digoxigenin using the DIG-HIGH PRIMR kit (Roche), following the manufacturer's instructions.

| Primer | Gene | Sequence 5'-3' (SEQ ID NOS 13-18 respectively in order of appearance) |
|---|---|---|
| TSFB1 | TSB1 | 5'-CTCATGGCCGCCGGATCTTGA-3' |
| TSBR1 | TSB1 | 5'-CTTGTCTCTCCATATCTTGAGCA-3' |
| GFPF1 | GFP | 5'-GGAGAAGAACTTTTCACTGGAGTTGTCCC-3' |
| GFPR1 | GFP | 5'-TAGTTCATCCATGCCATGTGTAATCCCAGC-3' |
| GUSF1 | GUS | 5'-AATAACGGTTCAGGCACAGC-3' |
| GUSR1 | GUS | 5'-CTGTGGAATTGATCAGCGTTG-3' |

---

The invention claimed is:

1. A genetic construct for the expression of a nucleic acid sequence in plant stomatal guard cells, said construct comprising the nucleic acid sequence functionally linked to the promoter of SEQ ID NO: 1, or to a fragment thereof having promoter activity, wherein said promoter fragment contains a sequence selected from the group consisting of: SEQ ID NO: 2, SEQ ID NO: 3, and SEQ ID NO: 4.

2. The construct of claim 1, wherein said promoter fragment contains SEQ ID NO: 2.

3. The construct of claim 1, wherein said promoter fragment contains SEQ ID NO: 3.

4. The construct of claim 1, wherein said promoter fragment contains SEQ ID NO: 4.

5. The construct of claim 1, wherein the nucleic acid sequence or a product encoded by said sequence is involved in the intracellular signalling pathway modulated by abscisic acid (ABA).

6. The construct of claim 5, wherein said nucleic acid sequence contains the coding sequence of Osml, Racl, Katl, Ostl, or Chll gene.

7. The construct of claim 5, wherein said nucleic acid sequence codes for an antisense RNA.

8. A plant expression vector containing the genetic construct according to claim 1.

9. The vector of claim 8, which is a bacterial plasmid, a bacterial artificial chromosome (BAC), a yeast artificial chromosome (YAC), a viral vector or a vector for *Agrobacterium*-mediated DNA transfer.

10. The vector of claim 8, which is a binary vector for *Agrobacterium*-mediated DNA transfer.

11. A monocotyledonous or dicotyledonous plant containing the vector according to claim 8.

12. A method for the expression of a nucleic acid sequence in plant stomatal guard cells, said method comprising, introducing into said plant stomatal guard cells the vector according to claim 8.

13. The method according to claim 12, wherein said sequence is involved in the regulation of stoma aperture/closure.

14. A method for regulating the expression of a nucleic acid sequence in a plant, which comprises introducing in said plant, in a vegetative or reproductive part thereof, the genetic construct according to claim 1.

15. A monocotyledonous or dicotyledonous plant containing the construct according to claim 1.

16. A method for the expression of a nucleic acid sequence in plant stomatal guard cells, said method comprising introducing into said plant stomatal guard cells the construct according to claim 1.

17. A method for regulating the expression of a nucleic acid sequence in a plant, which comprises introducing in said plant, in a vegetative or reproductive part thereof, the vector according to claim 8.

18. A genetic construct for the expression of a nucleic acid sequence in plant stomatal guard cells, said construct comprising the nucleic acid sequence functionally linked to the promoter of SEQ ID NO: 1.

* * * * *